(12) United States Patent
Sikdar et al.

(10) Patent No.: US 7,803,116 B2
(45) Date of Patent: Sep. 28, 2010

(54) TRANSCUTANEOUS LOCALIZATION OF ARTERIAL BLEEDING BY TWO-DIMENSIONAL ULTRASONIC IMAGING OF TISSUE VIBRATIONS

(75) Inventors: Siddhartha Sikdar, Seattle, WA (US); Yongmin Kim, Lake Forest Park, WA (US); Kirk Beach, Seattle, WA (US)

(73) Assignee: University of Washington through its Center for Commericalization, Seattle, WA (US)

( * ) Notice: Subject to any disclaimer, the term of this patent is extended or adjusted under 35 U.S.C. 154(b) by 989 days.

(21) Appl. No.: 10/574,133

(22) PCT Filed: Oct. 1, 2004

(86) PCT No.: PCT/US2004/032427

§ 371 (c)(1),
(2), (4) Date: Nov. 13, 2006

(87) PCT Pub. No.: WO2005/037060

PCT Pub. Date: Apr. 28, 2005

(65) Prior Publication Data

US 2007/0066895 A1    Mar. 22, 2007

Related U.S. Application Data

(60) Provisional application No. 60/508,554, filed on Oct. 3, 2003.

(51) Int. Cl.
*A61B 8/14* (2006.01)

(52) U.S. Cl. .................. 600/462; 600/437; 600/407; 600/465; 600/468

(58) Field of Classification Search ......... 600/437–461; 73/603; 604/19, 20
See application file for complete search history.

(56) References Cited

U.S. PATENT DOCUMENTS

| 5,194,291 | A | 3/1993 | D'Aoust et al. ............. 148/276 |
| 5,534,232 | A | 7/1996 | Denes et al. ........... 422/186.26 |
| 5,638,823 | A | 6/1997 | Akay et al. ................. 600/528 |
| 5,824,277 | A | 10/1998 | Campos ................... 423/242.1 |
| 5,840,028 | A | 11/1998 | Chubachi et al. ............ 600/437 |
| 5,882,302 | A | 3/1999 | Driscoll et al. |
| 5,919,139 | A * | 7/1999 | Lin ............................ 600/443 |
| 5,935,339 | A | 8/1999 | Henderson et al. ............. 134/1 |

(Continued)

FOREIGN PATENT DOCUMENTS

WO    WO 02/069805    12/2002

*Primary Examiner*—Long V Le
*Assistant Examiner*—Joel F Brutus

(57) ABSTRACT

An ultrasound based technique for detecting and imaging vibrations in tissue caused by eddies produced during bleeding through punctured arteries or from organs. A clutter signal, normally suppressed in conventional color flow imaging, is employed to detect and characterize local tissue vibrations, to detect internal bleeding in an image, or as an audible or palpable signal, or a readout. Using a tissue vibration image, the origin and extent of vibrations relative to the underlying anatomy and blood flow can be visualized in real time, enabling measurements of vibration amplitude, frequency, and spatial distribution. Bleeding rate can be determined from the frequency and amplitude of the vibrations. Signal processing algorithms usable to identify tissue vibrations from an ensemble of 2D ultrasound data include those based on phase decomposition, spectral estimation using eigendecomposition, and spectral estimation using autoregressive modeling for isolating vibrations from clutter, blood flow, and noise.

11 Claims, 8 Drawing Sheets

U.S. PATENT DOCUMENTS

| | | | |
|---|---|---|---|
| 5,951,476 A * | 9/1999 | Beach | 600/437 |
| 5,993,389 A | 11/1999 | Driscoll et al. | |
| 6,036,650 A | 3/2000 | Wu et al. | 600/462 |
| 6,200,539 B1 | 3/2001 | Sherman et al. | 422/186.04 |
| 6,406,759 B1 | 6/2002 | Roth | 427/562 |
| 6,626,855 B1 | 9/2003 | Weng et al. | 601/3 |
| 6,706,892 B1 | 3/2004 | Ezrin et al. | 548/548 |
| 6,709,407 B2 | 3/2004 | Fatemi | 600/559 |
| 6,875,176 B2 | 4/2005 | Mourad et al. | 600/442 |
| 2004/0002654 A1 | 1/2004 | Davidson et al. | 600/454 |
| 2004/0030268 A1 | 2/2004 | Weng et al. | 601/2 |
| 2005/0065436 A1 | 3/2005 | Ho et al. | 600/431 |
| 2008/0045864 A1 | 2/2008 | Candy et al. | 601/2 |
| 2008/0200815 A1 | 8/2008 | Van Der Steen et al. | 600/467 |

* cited by examiner

TRANSCUTANEOUS LOCALIZATION OF ARTERIAL BLEEDING BY TWO-DIMENSIONAL ULTRASONIC IMAGING OF TISSUE VIBRATIONS

GOVERNMENT RIGHTS

This invention was funded at least in part with grants from the U.S. Office of Naval Research (ONR) (Award Nos. N00014-96-1-0630, N00014-01-G-0460, and N00014-99-1-0982), and grants from the U.S. Department of Defense (DoD) (ARMY MRMC Award Nos. DAMD17-02-2-0014, and DAMD17-00-2-0063), and the U.S. government may have certain rights in this invention.

FIELD OF THE INVENTION

This invention generally relates to a method for identifying tissue vibrations using an ensemble of two-dimensional (2D) ultrasound data acquired with an ultrasound transducer, and more specifically, to a method and system for identifying bleeding sites within a body of a patient in real time, based upon the tissue vibration that occurs at the sites, so that arterial bleeding and bleeding from organs can readily be localized in an image.

BACKGROUND OF THE INVENTION

Internal bleeding is a significant cause of death in cases of trauma, and rapid and effective diagnosis of patients with uncontrolled bleeding has long been recognized as an important goal to lower mortality and morbidity. Currently, internal bleeding is diagnosed using angiography, Computed Tomography (CT), diagnostic peritoneal lavage, B-mode ultrasound, and exploratory laparotomy, while surgical intervention is the most common treatment option. The detection of a bleeding site (i.e., diagnostic imaging) and the closure of a bleeding wound should preferably be accomplished as quickly as possible to minimize blood loss in a patient and reduce mortality and morbidity associated with such blood loss.

Advances in duplex and color-flow ultrasound in the last two decades have had a significant clinical impact on vascular diagnosis. For example, the use of Doppler ultrasound has been shown to be effective for targeting a bleeding site, as disclosed in a paper by R. W. Martin, S. Vaezy, P. Kaczkowski, G. Keilman, S. Carter, M. Caps, K. W. Beach, M. I. Plett, and L. A. Crum, entitled "Hemostasis of punctured vessels using Doppler-guided high-intensity ultrasound," *Ultrasound Med. Biol.*, vol. 25, pp. 985-990, 1999. However, this technique suffers from the disadvantage of imaging a limited region of interest. Although color-flow ultrasound can image a large region of interest, currently it lacks sufficient sensitivity for diagnosing internal bleeding, due to weak scattering from blood and the slow flow velocity of blood bleeding from a wound, especially in the case of deep bleeds and organ bleeds. In a paper by X. Shi, R. W. Martin, S. Vaezy, and L. A. Crum, entitled "Quantitative investigation of acoustic streaming in blood," *J. Acoust. Soc. Am.*, vol. 111, pp. 1110-1121, 2002, the use of acoustic streaming is proposed for distinguishing between stagnant blood and tissue using color-flow images. However this paper does not suggest how to detect a bleeding site with acoustic streaming. The use of contrast agents has also shown to be promising for localizing active bleeding sites, as discussed in a paper by J-B Liu, D. A. Merton, B. B. Goldberg, N. M. Rawool, W. T. Shi, and F. Forsberg, entitled "Contrast-enhanced two- and three-dimensional sonography for revaluation of intra-abdominal hemorrhage," *J. Ultrasound Med*, vol. 21, pp. 161-169, 2002. Yet, the use of contrast agents is time-consuming and can sometimes be dangerous.

Each of these prior art techniques for detecting bleeding is unable to provide efficient real-time images in which the location of a bleeding site can be rapidly identified. Also, as discussed in greater detail below, simply using conventional color-flow data for imaging a site cannot readily distinguish between pooled blood and bleeding at the site. Accordingly, it is necessary to develop a new method for rapid diagnosis of internal bleeding.

Physical examination is an important element of the initial assessment of a trauma patient with suspected internal bleeding. If an audible "bruit" or a palpable "thrill" is found upon physical examination, further diagnostic tests for internal bleeding or surgical intervention are often recommended. It has now been established that bruits and thrills are produced by the forces exerted on vessel walls by eddies created as blood flows from a high-pressure region to a low-pressure region through a narrow orifice. The pressure fluctuations in eddies cause local vibrations in the vessel wall and surrounding tissue and manifest either as bruits or thrills at the skin surface. The power spectrum of the vibrations exhibits a frequency peak called the "break frequency," which is directly related to the diameter of the orifice and the local flow velocity through the Strouhal number. In conventional color-flow ultrasound images, tissue vibrations from abnormal blood flow produce characteristic speckled artifacts in the surrounding tissue. But, these artifacts are difficult to interpret and are not quantitative. Tissue vibrations have been previously studied using one-dimensional (1D) pulsed Doppler ultrasound, and the prior art includes disclosure of a wavelet-based method for detecting and characterizing arterial vibrations in internal bleeding (M. I. Plett, "Ultrasonic arterial vibrometry with wavelet-based detection and estimation," *PhD. dissertation*, Univ. of Washington, 2000). However, this pulsed Doppler-based technique also has a limited field of view, and is along a single scan line. Furthermore, as disclosed in this paper, the processing was done off-line, so it was not possible to create images interactively in real time.

Accordingly, it would be desirable to develop a new tissue vibration detection and imaging mode for ultrasound instruments in which vibrations produced by blood flow eddies can be detected and color-coded according to their amplitude and frequency and overlaid on a B-mode and/or a color-flow image in real time. The tissue vibration imaging mode might then be used for locating the origin of the vibration more precisely, relative to the patient's anatomy and/or for obtaining simultaneous information about vibrations and the underlying blood flow. Acoustic hemostasis using High Intensity Focused Ultrasound (HIFU) is a promising new technique for stopping internal bleeding without invasive surgical intervention. For effective targeting and monitoring of hemostasis, non-invasive real-time localization of a bleeding site in real time is essential. This new technique might thus be used both for diagnostic determination of a bleeding site, and optionally, in conjunction with HIFU or other desired therapy, for localizing the bleeding site in real time, so that therapy might be effectively applied to stop the bleeding as indicated in the U.S. Pat. No. 6,083,159, "Methods and devices for providing acoustic hemostasis", U.S. Pat. No. 5,993,389, "Devices for providing acoustic hemostasis", and U.S. Pat. No. 5,882,302, "Methods and devices for providing acoustic hemostasis".

SUMMARY OF THE INVENTION

This invention was developed to localize a bleeding site by imaging tissue vibrations caused by arterial bleeding into a free space. Sounds caused by these vibrations (bruits) are sometimes audible using a stethoscope or palpable at the skin surface and are indicative of internal bleeding in a trauma patient. Previously, a Doppler-based algorithm might have been used for offline analysis of vibrations along a single ultrasound scan line. In contrast, this invention employs an algorithm that processes an ensemble of 2D ultrasound data for detecting and imaging tissue vibrations in a relatively large region of interest. The algorithm has been implemented in a programmable ultrasound system to study the usefulness of tissue vibrations in real-time localization of bleeding sites in animals and has been shown to be very effective for this purpose.

The vibration imaging algorithm uses an ensemble of 2D ultrasound data acquired during conventional ultrasonic imaging and utilizes the clutter signal, which is normally suppressed in conventional color-flow imaging, to detect and characterize tissue vibrations. Three signal processing algorithms have been developed that are suitable for this purpose, including one based on phase decomposition, a second based on spectral estimation using eigendecomposition, and a third based on spectral estimation using autoregressive modeling for isolating vibrations from clutter, blood flow, and noise in an ensemble of 2D ultrasound data.

Real-time tissue vibration imaging has been implemented at frame rates, for example, of 10 frames/second, on an ultrasound system with a software-programmable signal and image processing back-end. The preliminary results confirm that vibrations produced as a result of arterial bleeding can be detected and imaged with this invention. The vibration amplitude is expected to be the largest near the site of the bleeding, and this fact can be used to localize a bleeding site quickly and non-invasively. The strong backscattered ultrasonic echoes from tissue vibrations can improve visualization of internal bleeding sites that are otherwise hard to image due to weak scattering from blood.

Potentially, this new tissue vibration imaging technology could be useful in a variety of devices and clinical settings. For example, a low-cost portable screening device with tissue vibration detection functionality could be beneficially employed by paramedics and trauma centers to localize bleeding in patients. In addition, a tissue vibration imaging mode on high-end ultrasound systems can augment duplex ultrasound for enhanced diagnostic capability. The detected tissue vibrations indicative of internal bleeding could be presented as an audible signal in a manner recognizable to a person trained to listen to bruits using a stethoscope or as a palpable signal recognizable to a person trained to detect palpable thrills.

One aspect of the invention is directed to a method for detecting and localizing internal bleeding using an ensemble of 2D ultrasound data by detecting and characterizing tissue vibrations caused by blood flow eddies at the bleeding site. The method includes the step of processing an ensemble of 2D ultrasound data, producing a tissue motion spectrum signal at a site. The tissue motion spectrum signal is then filtered to produce a filtered signal from which any contribution to the tissue motion from a source other than bleeding at the site has been substantially minimized, producing a tissue vibration signal. A vibration image is displayed using the filtered signal and indicates a location of bleeding at the site.

One approach for processing the ensemble of 2D ultrasound data comprises the steps of estimating a correlation matrix from the ultrasound data, and carrying out an eigendecomposition of the correlation matrix to identity a signal subspace and a noise subspace. A frequency of the dominant vibration components in the signal subspace and the noise subspace are then estimated, and based upon that estimate, a vibration amplitude estimate and a vibration frequency estimate are determined. At least one of the vibration amplitude estimate and the vibration frequency estimate comprises the tissue vibration signal.

A second approach for processing the ensemble of 2D ultrasound data includes the step of computing reflection coefficients from the ultrasound data. Linear prediction filter coefficients are computed from the reflection coefficients. A power spectrum is estimated, and the peaks in the power spectrum are detected. Based upon the estimate of the power spectrum and the peaks, a vibration amplitude estimate and a vibration frequency estimate are determined. At least one of the vibration amplitude estimate and the vibration frequency estimate again comprises the tissue vibration signal.

In yet another approach for processing the ensemble of 2D ultrasound data, a mean clutter velocity is estimated from the ultrasound data using autocorrelation. The ensemble of 2D ultrasound data are down-mixed with the mean clutter velocity, producing a down-mixed signal. A phase of the down-mixed signal and a mean phase of the down-mixed signal are determined, and the mean phase is subtracted from the phase of the down-mixed signal, producing a residual phase. The residual phase is then decomposed into its dominant components. By applying energy and frequency thresholds, any contribution to the tissue vibration due to noise and blood flow are substantially suppressed, yielding an estimate of vibration amplitude and vibration frequency of tissue due to bleeding.

The step of decomposing the residual phase preferably comprises the steps of estimating a correlation matrix from the residual phase, and performing an eigendecomposition of the correlation matrix to determine the dominant components.

The step of filtering preferably comprises the step of filtering out clutter and noise at frequencies that are substantially lower than an expected frequency range of tissue vibrations corresponding to bleeding at the site, and also preferably includes the step of filtering out noise that is at frequencies, which are substantially higher than an expected frequency range of tissue vibrations corresponding to bleeding at the site.

In addition, the method can include the step of confirming that vibrations displayed in the vibration image correspond to bleeding at the site, by placing a Doppler sample volume at a location of the tissue vibration determined from the tissue vibration image. In this step, the tissue vibration spectrum determined from a relatively larger number of samples (typically, 64-512) available using Doppler data can be employed to confirm the tissue vibration detected from only a few ensemble (typically, 6-16) of 2D ultrasound data.

The step of displaying the vibration image preferably comprises the step of displaying at least one of a vibration amplitude image and a vibration frequency image of the site. Because of its efficiency, the method can include the step of displaying the vibration image in connection with an underlying anatomy of the site (i.e., the B-mode grayscale image), substantially in real time.

Another aspect of the present invention is directed to apparatus for detecting and localizing bleeding at an internal site using an ensemble of 2D ultrasound data. The apparatus includes an ultrasound transducer for transmitting ultrasound pulses toward the internal site and receiving ultrasound data from scatterers at the internal site, including tissue that is vibrating due to bleeding at the site. In one embodiment, a front-end system controls the ultrasound pulses produced by the ultrasound transducer and demodulates the echoes received by the ultrasound transducer, producing a color-flow signal having both in-phase and quadrature components. The apparatus also includes a back-end system to receive the color-flow signal from the front-end system and which includes a tissue vibration processor. The front and back-end systems can optionally be combined into a single unit, or one or more parts of these systems can be operating remotely from other parts of these systems. The tissue vibration processor processes the ultrasound signal to estimate tissue vibrations caused by bleeding, producing a tissue vibration signal. In one embodiment, the tissue vibration signal is converted to an image signal by the back-end system. A display is coupled to the back-end system to receive the image signal, to display a tissue vibration image in which bleeding at the internal site is indicated. Optionally, the display could be decoupled from the tissue vibration detection and identification apparatus. For example, the display can be located physically in a hospital, while the tissue vibration detection and identification apparatus is located physically at another location, such as in an ambulance. Also, instead of a visible display, the result of tissue vibration detection and identification can be presented as an audible or a palpable output indicating tissue vibrations. The tissue vibration signal can also be interpreted by an automated algorithm to indicate internal bleeding, and the result of the automated interpretation presented as an electronic readout. Generally, the functions performed by the apparatus are consistent with the steps of the method described above.

BRIEF DESCRIPTION OF THE DRAWING FIGS.

The foregoing aspects and many of the attendant advantages of this invention will become more readily appreciated as the same becomes better understood by reference to the following detailed description, when taken in conjunction with the accompanying drawings, wherein.

Figure 5C:
Figure 5B:
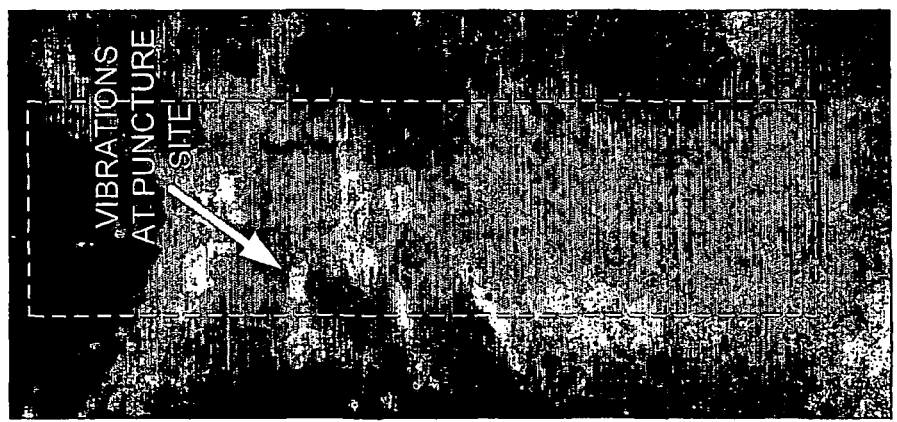
Figure 5A:
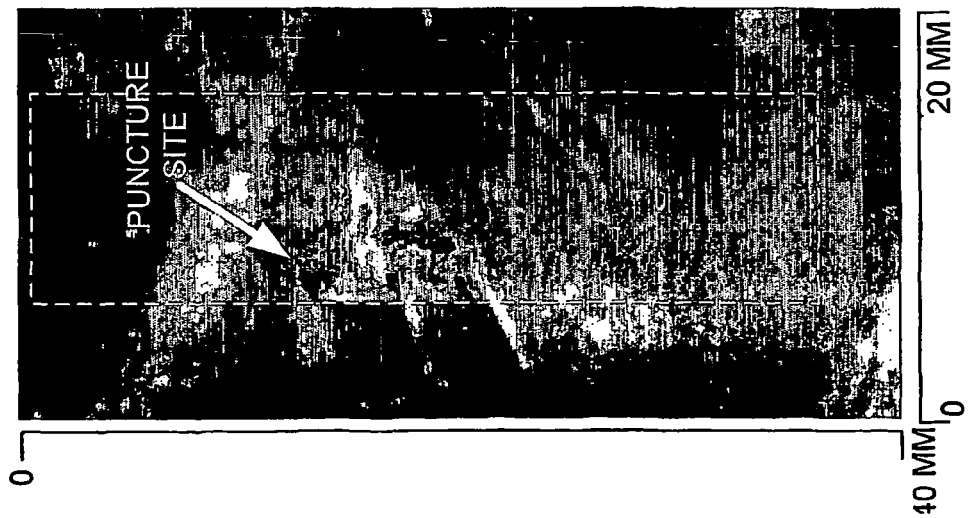
Figure 6C:
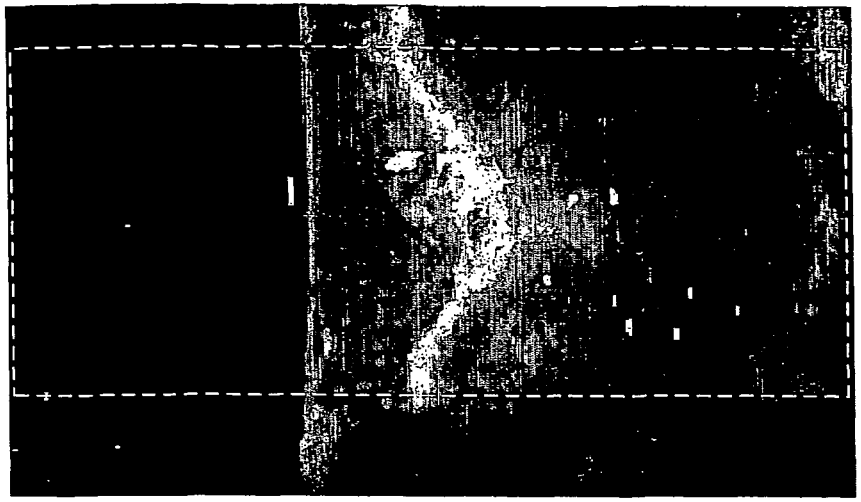
Figure 6B:
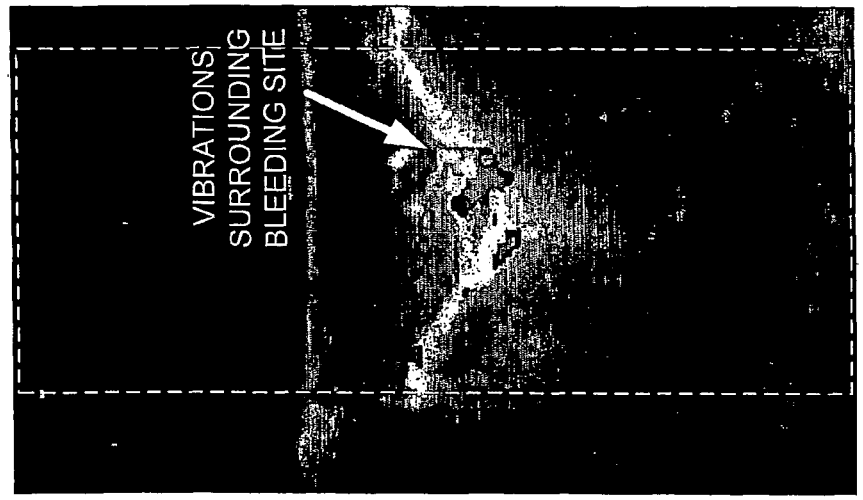
Figure 6A:
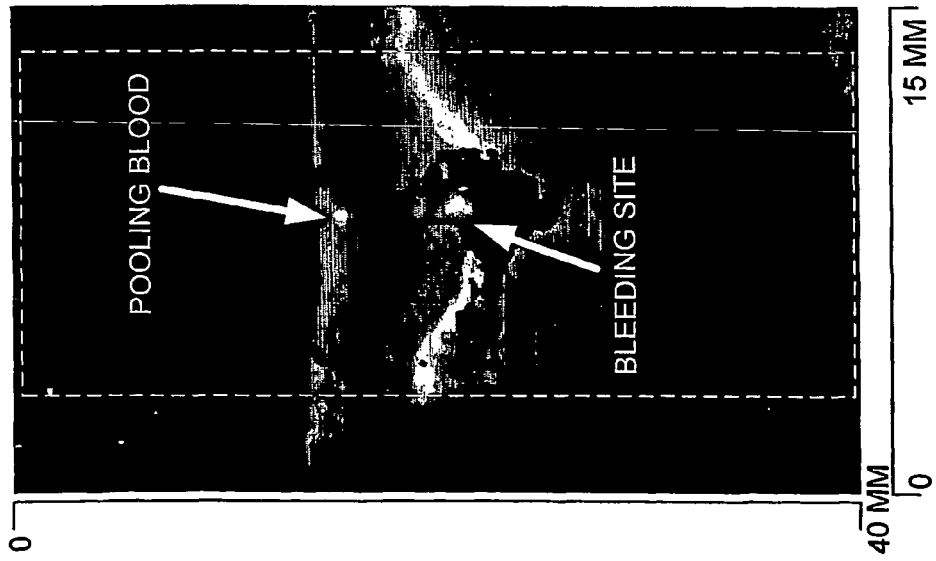
Figure 7C:
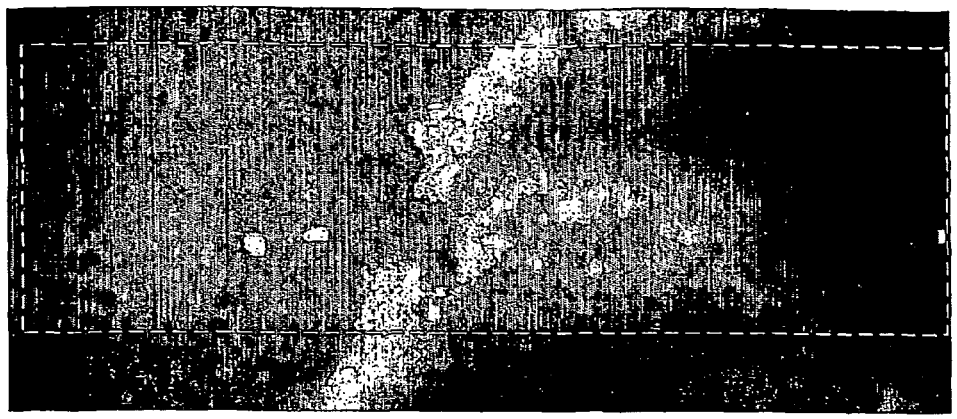
Figure 7B:
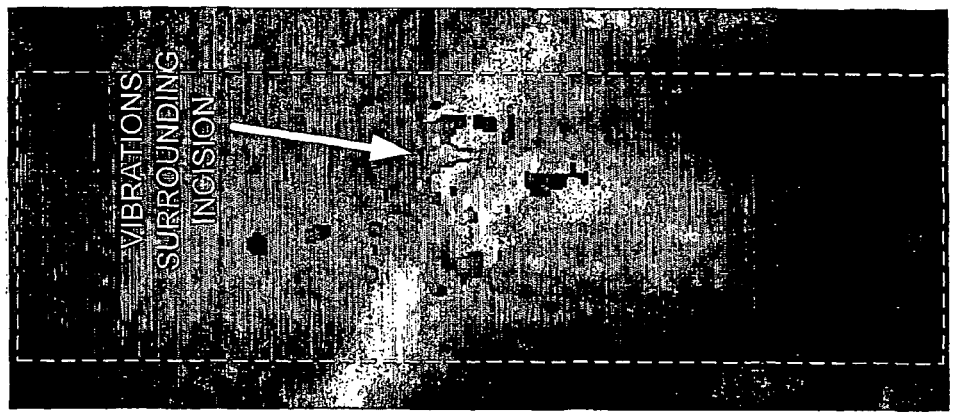
Figure 7A:
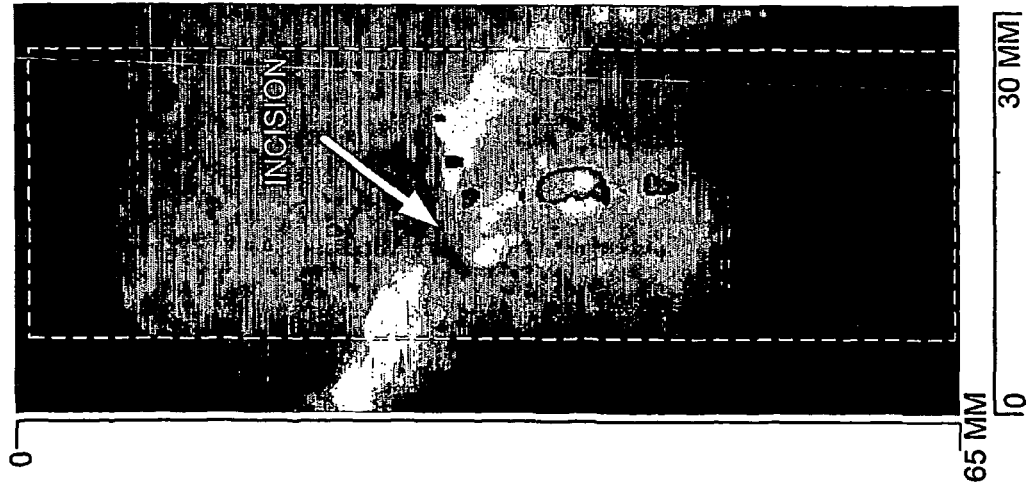

FIGS. 5A, 5B, and 5C are respectively a color-flow image of a punctured femoral artery, a vibration amplitude image of the artery, and a vibration frequency image of the artery;

FIGS. 6A, 6B, and 6C respectively illustrate a color-flow image of an incised spleen, a vibration amplitude image of the spleen, and a vibration frequency image of the spleen; and FIGS. 7A, 7B, and 7C respectively illustrate a color-flow image of an incised liver, a vibration amplitude image of the liver, and a vibration frequency image of the organ.

DESCRIPTION OF THE PREFERRED EMBODIMENT

Tissue Vibration Imaging System

Figure 1:
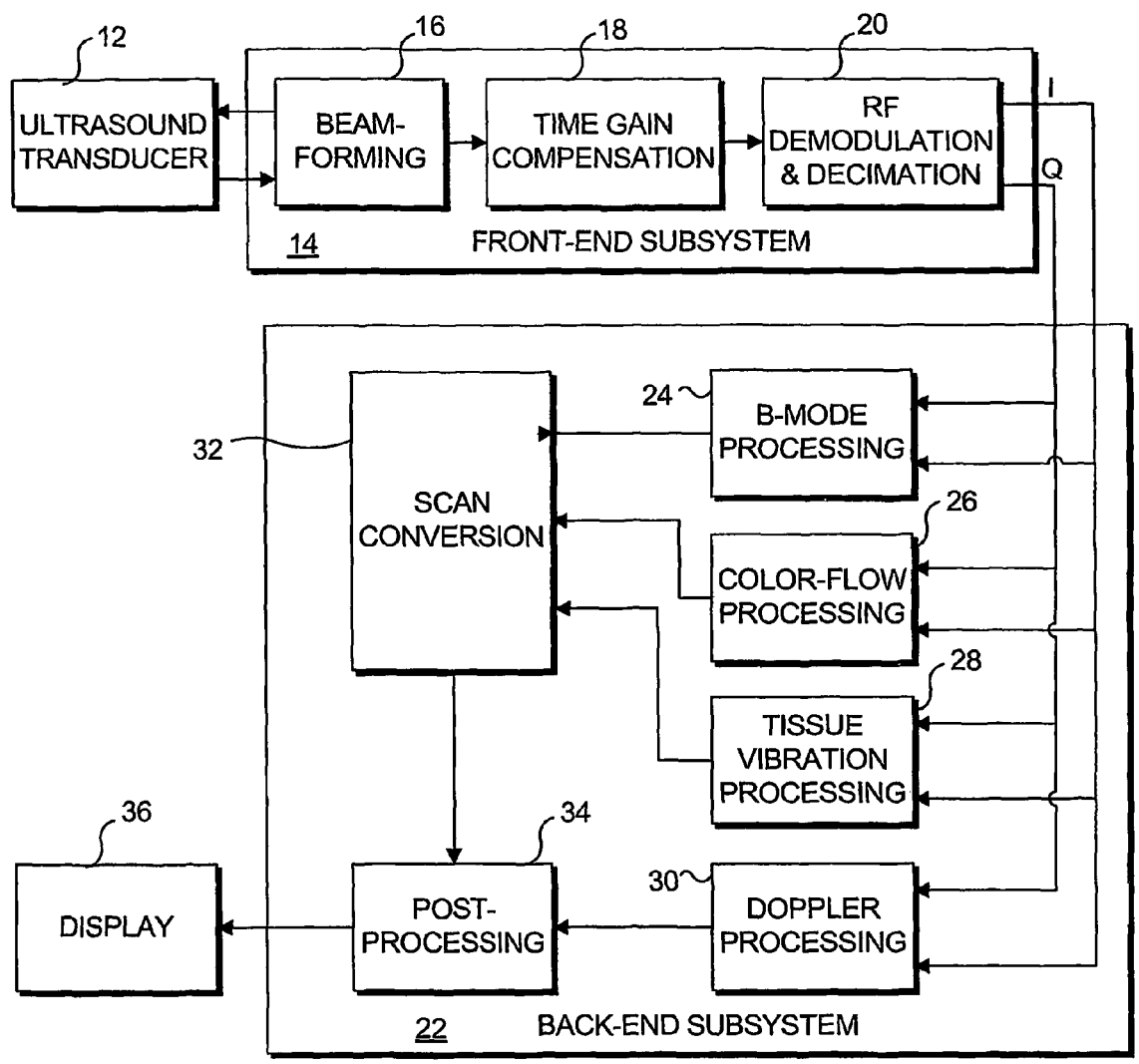
FIG. 1 is a functional block diagram of an exemplary ultrasound system that is suitable for carrying out tissue vibration imaging in accord with the present invention.

FIG. 1 is a block diagram illustrating an ultrasound system 10, which is generally similar to a conventional ultrasound system, but which has been modified to include tissue vibration imaging and is thus usable in practicing the present invention. Ultrasound system 10 includes an ultrasound transducer 12 that transmits a signal, which is modulated with a carrier frequency, typically 1 MHz-15 MHz, using multiple cycles (i.e., 2-20 cycles). The transmitted signal is reflected by scatterers (not shown) along the beam path and is received after a time delay, which depends upon the distance of the scatter from the transducer. In an acquisition stage, the acoustic echoes received from the tissue are converted to electrical signals by the transducer, and these signals are digitized by analog-to-digital converters (not separately shown). A front-end subsystem 14 includes a beam former 16 that performs dynamic focusing, apodization, and steering of both transmitted and received ultrasonic waveforms. Also included in front-end system 14 are a time-gain-compensation (TGC) circuit 18 that amplifies signals with a variable gain that is proportional to the depth within tissue, and a radio frequency (RF) demodulator and decimator 20 that digitally removes the high frequency carrier by quadrature demodulation and decimation, providing both in-phase (I) and quadrature (Q) samples, which may be represented as a complex quantity, $I(t)+jQ(t)$. The acquired quadrature ensemble (or color-flow) data are then processed in a back-end subsystem 22, depending on the one (or more) ultrasound mode(s) that is/are selected, e.g., B-mode, color-flow mode, tissue vibration mode, and Doppler mode.

For producing anatomic images of tissue, the signal of interest is the envelope of $I(t)+jQ(t)$. A B-mode processor 24 computes the magnitude of the echo, $B_a(t)=\sqrt{I^2(t)+Q^2(t)}$ and compresses the dynamic range to make it suitable for display as a grayscale image on a monitor. The time delay introduced by the scatterers is reflected in the phase of the complex quantity $I(t)+jQ(t)$. Thus, the phase of the complex received signal provides an estimate of the instantaneous position of the scatterer. By monitoring the change of phase over time, the displacement and velocity of the scatterer can be estimated. In color-flow imaging, multiple pulses (commonly from 6 to 16 pulses) are transmitted and received along each scan line at a rate known as the pulse repetition frequency (PRF). A collection of received temporal samples from each spatial location is thus called an "ensemble." A color-flow processor 26 estimates the blood flow velocity from the ensemble of data by estimating the phase difference between the adjacent temporal samples, typically using an autocorrelation algorithm. A 2D image is created by acquiring multiple samples from different spatial locations. In Doppler mode which is implemented by a Doppler processor 30, scanning is performed along a single scan line, and a spectrum of the blood velocity from a single spatial location is estimated from a substantially larger ensemble of data (typically, data from 64-512 pulses). Before displaying the processed image frame on a raster monitor or display 36, scan conversion is performed by a scan converter circuit 32, which converts the acquired ultrasound data from polar coordinates to the Cartesian coordinates used by the raster display. Post processing may optionally be applied by a post-processing circuit 34, to improve the quality of the displayed image, as well as to combine the anatomy and flow images on the display.

A tissue vibration processor 28 that is used to process the ultrasound data in the present invention is shown in FIG. 1. The ultrasound data acquisition for tissue vibration processing and imaging is the same as that used for color-flow, so that quadrature data ensemble or color-flow data are input to the tissue vibration processor. However, instead of estimating blood flow velocity from these data, the tissue vibration processor estimates the instantaneous displacement of the scattering tissue from the phase of the complex received signal. This tissue motion is referred to as clutter in conventional color-flow imaging and is suppressed using clutter filters. Typically, cardiac pulsation, respiration and transducer motion each can contribute to an observed displacement or motion of tissue. Such motion is at a low frequency of a few Hertz or less. When internal bleeding is present, the tissue vibrates locally with a frequency ranging from a few tens of Hertz to a few hundred Hertz. By analyzing the frequencies of the different components of tissue motion, vibrations caused by bleeding may be distinguished from clutter caused by other sources of movement. The tissue vibration processor performs this analysis by decomposing the tissue motion into the dominant motion components and identifying any motion components that appear to be at a frequency higher than that of cardiac pulsation.

It is contemplated that tissue vibration processor 28 can be implemented as an additional fixed-function circuit board or application specific integrated circuit (ASIC) in conventional ultrasound machines. Optionally, the tissue vibration processor can be combined with color-flow processor 26, since both process the same data ensemble. A standalone tissue vibration imaging device can be implemented with front-end subsystem 14, B-mode processor 24, tissue vibration processor 28, and scan converter 32. Those of ordinary skill in the art will appreciate that the tissue vibration processor can be implemented in software/hardware using one or more digital signal processors (DSPs) or alternatively, in an ASIC, or even on a conventional general purpose processor chip that access machine language instructions stored in a memory accessed by the processor to carry out the processing steps of the tissue vibration processor.

The computational power of ultrasound machines has increased significantly in recent years, benefiting from advances in processor technology. Thus, the additional computational burden of the tissue vibration imaging algorithms discussed below can be reasonably supported in modern ultrasound machines. Previously, a programmable ultrasound signal and image processing system suitable for use as the tissue vibration processor was developed using a new generation of high-performance multimedia processors to support all of the conventional processing modes, such as B, M, color-flow, and Doppler in software (Sikdar S, Shamdasani V, Gong L, Managuli R, Hayashi T, Mitake T, Kim Y. "*A single mediaprocessor-based programmable ultrasound system*," IEEE Trans Inf. Tech. Biomed 2003; 7:64-70), and subsequently, was shown to be useful in implementing tissue vibration processing in accord with the present invention. The main strength of a programmable system is the ease of development of new modes and applications such as tissue vibration imaging without the need for hardware modifications to conventional ultrasound machines. Integrated tissue vibration imaging using the software-programmable ultrasound system has thus been effectively and beneficially used for real-time visualization of vibrations in 2D ultrasound scans.

Algorithms for Tissue Vibration Imaging

In conventional color-flow imaging, the velocity of blood flow is estimated by computing the average phase difference between multiple ultrasound echoes (typically 6-16 pulses) that are received from a sample volume. Echoes from moving tissue tend to have a significantly higher signal strength (typically 40 dB-60 dB higher), compared to the weak scattering from blood, and also have lower velocities. This high amplitude and low frequency tissue signal is commonly referred to as clutter and tends to bias the estimated blood flow velocity. Thus, clutter is suppressed using appropriate filters in conventional color flow imaging. The main components of clutter are cardiac pulsation, respiration, and transducer movement. When blood flow eddies are present, any local tissue vibrations, e.g., those caused by the blood flow eddies at a bleeding site, will also be part of this clutter and would normally be suppressed in conventional ultrasound processing systems.

The present invention separates the tissue vibrations from the remaining clutter and flow signals. In achieving this function, it was recognized that the tissue vibrations and clutter produce statistically independent signals that have different frequency content. While clutter due to cardiac pulsation and breathing typically occurs at 1 Hz or less, tissue vibrations typically occur at 50 Hz or more. Other noise sources are at substantially higher frequencies. Scattering from tissue is typically more coherent compared to the scattering from blood, because the tissue scatterers are more tightly bound together and tend to move as a group. Thus, compared to the clutter from other sources and tissue vibration signals, the blood flow signal typically has a much greater frequency bandwidth. Due to its weak signal strength and greater bandwidth, blood flow signals may be considered as noise compared to the stronger and more coherent tissue vibration signals for purposes of this invention. Therefore, tissue vibrations can be distinguished from clutter and blood flow based on spectral analysis. Spectral analysis of the phase of the received ultrasound echo can be used to separate the components of the scatterer motion, ignoring the scattered signal strength, whereas spectral analysis of the complex ultrasound echo considers both the signal strength and the motion components.

Due to the limited number of temporal ultrasound samples (6-16 pulses) preferably used in the present invention, conventional Fourier transform and filtering approaches lack sufficient resolution for separating the signals. Therefore, this invention employs high-resolution spectral estimation techniques to carry out this function. Two high-resolution spectral estimation techniques were identified as suitable for this purpose, including eigendecomposition-based spectral estimation, which models the signal as an optimum set of orthogonal components, and autoregressive spectral estimation, which models the signal as the output of an autoregressive linear prediction filter driven by white Gaussian noise. Accordingly, three signal processing algorithms were developed for isolating tissue vibrations. The first algorithm is based on an eigendecomposition-based spectral analysis of the phase, of the received ultrasound echo; the second algorithm is based on an eigendecomposition-based spectral analysis of the complex ultrasound echo; and, the third algorithm is based on an autoregressive spectral analysis of the complex ultrasound echo. Since eigendecomposition is a computationally-intensive operation, an approximate eigendecomposition utilizing iterative QR factorization is used to develop a computationally-efficient algorithm.

Signal Model

To model the received signal from vibrating tissue, the tissue being imaged is approximated with S point scatterers having uniform motion and randomly distributed at locations $(\vec{r}_s=[r_s]\hat{e}_r+[\psi_s]\hat{e}_\psi+[\phi_s]\hat{e}_\phi)$, s=1 . . . S, in a sample volume where $(\hat{e}_r, \hat{e}_\psi, \hat{e}_\phi)$ denote the unit direction vectors in spherical coordinates. The instantaneous position of the scatterers, $v(\vec{r}, t)$, is given by:

$$v(\vec{r}, t) = \sum_s \delta(\vec{r} - \vec{r}_s(t)) \quad (1)$$

$$\vec{r}_s(t) = [r_s - d_r(t)]\hat{e}_r + [\psi_s - d_\psi]\hat{e}_\psi + [\phi_s - d_\phi]\hat{e}_\phi$$

where $(d_r(t), d_\psi(t), d_\phi(t))$ denote the displacement as a function of time. If the scattering from the sample volume is uniform with $\alpha$ as the average scattering coefficient, then the scattering function of the sample volume is $\alpha v(\vec{r}, t)$. The complex received signal from the sample volume, $y(\tau, t)$, can then be modeled as a convolution of the pulse echo spatial impulse response, $h_{pe}(\vec{r}, \tau)$, of a single point scatterer, the temporal response of the transducer, $x(\tau)$, and the scattering function, $\alpha v(\vec{r}, t)$.

$$y(\tau, t) = h_{pe}(\vec{r}, \tau) *_\tau x(\tau) *_r \alpha v(\vec{r}, t) + n(\tau, t) \quad (2)$$

$$x(\tau) = x_0(\tau) e^{j 2\pi f_0 \tau}$$

where the time indices $\tau$ and t refer to "fast" time and "slow" time, respectively, $f_0$ is the center frequency of the transducer, and $n(\tau, t)$ is white thermal noise. Combining Eqs. (1), (2), and (3) results in:

$$y(\tau, t) = \alpha \sum_x h_{pe}\left(\vec{r}_x(t), \tau - \frac{2(r_s - d_r(t))}{c}\right) \quad (3)$$

$$x_0\left(\tau - \frac{2(r_s - d_r(t))}{c}\right) e^{j 2\pi f_0 \left(\tau - \frac{2(r_s - d_r(t))}{c}\right)} + n(\tau, t)$$

where c is the speed of sound and $$\frac{2(r_s - d_r(t))}{c}$$

is the two-way pulse propagation time between the transducer and each point scatterer. The scatterer displacement for vibrations is small compared to the spatial size of the pulse echo spatial impulse response and the envelope of the transducer response. Thus, the "slow" time variations in the first two terms may be neglected and Eq. (3) can be simplified to:

$$y(\tau, t) = \left\{ \alpha \sum_s h_{pe}\left(\vec{r}_s, \tau - \frac{2r_s}{c}\right) x_0\left(\tau - \frac{2r_s}{c}\right) e^{j 2\pi f_0 \left(\tau - \frac{2r_s}{c}\right)} \right\} \quad (4)$$

$$e^{j 2\pi f_0 \frac{2d_r(t)}{c}} + n(\tau, t)$$

$$= A(\tau) e^{j 2\pi f_0 \frac{2d_r(t)}{c}} + n(\tau, t)$$

where $A(\tau)$ is the complex amplitude of the scattered signal. It is apparent that the complex received signal is phase modulated with the instantaneous radial displacement.

If the scatterers in the sample volume are all vibrating radially in a simple harmonic fashion with peak displacement $a_0$ and frequency $f_{vib}$, the tissue displacement due to cardiac pulsation, breathing, and other tissue movement (i.e., clutter or noise) relative to the transducer is $d_{tiss}(t)$. This motion will hereinafter be referred to as the "clutter motion." Then, the combined displacement can be considered to be a superposition, as follows:

$$d_r(t) = d_{tiss}(t) + a_0 \sin(2\pi f_{vib} t) \quad (5)$$

An ensemble of ultrasound pulses is transmitted in the same direction at a rate known as the pulse repetition frequency (PRF). Then, the complex received signal from the $m^{th}$ pulse transmission, $y(\tau, m)$, is:

$$y(\tau, m) = A(\tau) e^{j 2\pi f_0 \left( \frac{2 d_{tiss}(m T_{PRF})}{c} + \frac{2 a_0 \sin(2\pi m T_{PRF} f_{vib})}{c} \right)} + n(\tau, m) \quad (6)$$

where $T_{PRF}$ is the pulse repetition interval. The Fourier transform of the phase-modulated complex received signal is a Bessel series:

$$Y(\tau, f) = A(\tau) \left\{ \mathcal{F}\left(e^{j 2\pi f_0 \frac{2 d_{tiss}(m T_{PRF})}{c}}\right) *_f \mathcal{F}\left(e^{j 2\pi f_0 \frac{2 a_0 \sin(2\pi m T_{PRF} f_{vib})}{c}}\right) \right\} + N(\tau, f) \quad (7)$$

$$= A(\tau) \left\{ c(f) *_f \sum_{n=-\infty}^{n=\infty} j^n J_n(\beta) \delta(f - 2\pi n T_{PRF} f_{vib}) \right\} + N(\tau, f)$$

$$= A(\tau) \sum_{n=-\infty}^{n=\infty} j^n J_n(\beta) c(f - 2\pi n T_{PRF} f_{vib}) + N(\tau, f)$$

where $J_i$ are Bessel functions of the first kind, $$\beta = \frac{4\pi f_0 a_0}{c},$$

$\delta$ is the Dirac delta function, and $c(f)$ is the spectrum of the clutter motion (the clutter spectrum), and $N(\tau, f)$ is the noise spectrum.

Figure 2:
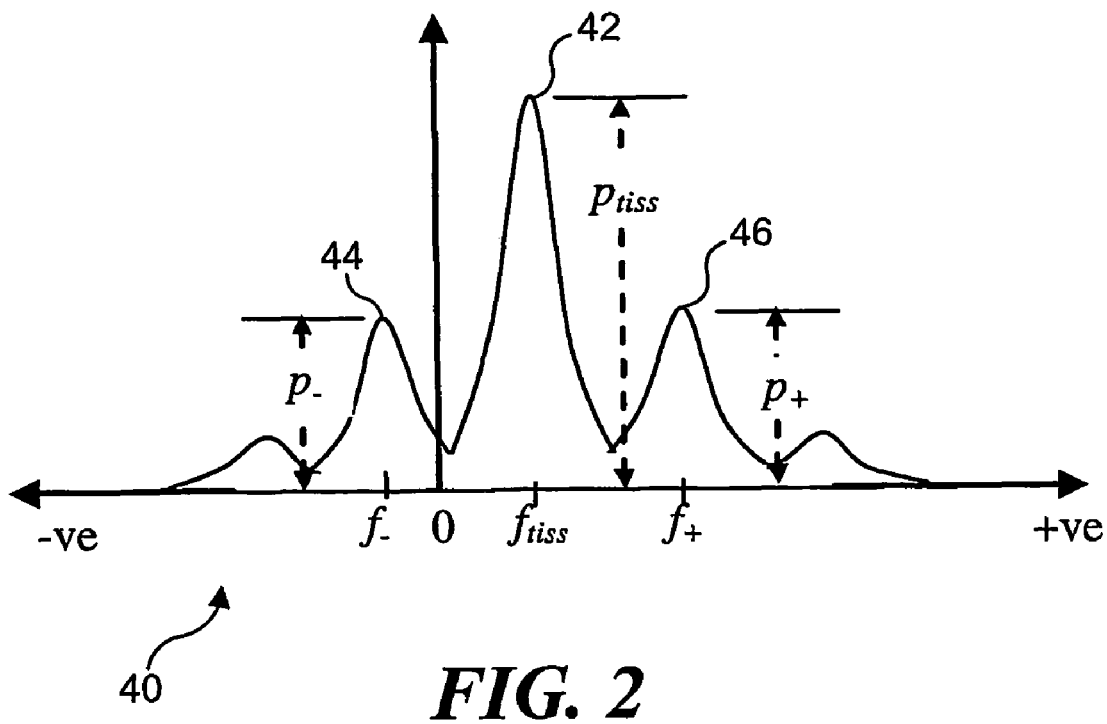
FIG. 2 is a graph of an expected Doppler spectrum (i.e., frequency vs. power) from a vibrating sample volume.

FIG. 2 illustrates a typical power spectrum 40 of the ultrasound signal when a tissue vibration is present. The spectrum includes multiple copies of the clutter spectrum separated by the vibration frequency, as indicated by Eq. (8), which is presented below. A low frequency peak 42 at $f_{tiss}$ corresponds to the clutter spectrum, while symmetric peaks $f_-$ and $f_+$ indicated respectively by reference numbers 44 and 46 correspond to vibration, and $p_{tiss}$, $p_+$, and $p_-$ are the corresponding peak powers. The frequency peaks at $f_+$ and $f_-$ are referred to herein as a "matching pair." For small-amplitude vibrations, higher-order terms can be ignored; thus, most of the spectral energy will be present in the three frequency peaks, $f_-$, $f_{tiss}$, and $f_+$, respectively. Since, $$\left| \frac{J_1(\beta)}{J_0(\beta)} \right| \approx \beta,$$

the ratio of the power in the frequency peaks can provide an estimate of the vibration amplitude. Therefore, the vibration frequency and amplitude may be estimated from the power spectrum as follows:

$$\hat{f}_{vib}^{power} = \left|\frac{f_+ - f_-}{2}\right|; \hat{a}_{vib}^{power} = \frac{c}{4\pi f_0}\sqrt{\frac{p_+ + p_-}{2p_{tiss}}}; \quad (8)$$

These estimators are referred to herein as the "spectral frequency estimator" and the "power ratio amplitude estimator." Alternatively, the vibration frequency and amplitude may be estimated from the residual phase $\{\phi(k)\}_{k=1}^{E}$ of the ultrasound signal after suppressing the effects of clutter motion. A coarse computationally-efficient estimate of the frequency of the dominant components, $\hat{f}_{vib}$, can be obtained by counting the zero crossings, $N_{zero}$, in the residual phase. This estimate can be further refined by interpolating the residual phase to compute the mean period of oscillation. The vibration amplitude may be estimated by the variance of the residual phase. These estimators are defined as follows:

$$\hat{f}_{vib}^{phase} = \left|\frac{f_+ - f_-}{2}\right|; \hat{a}_{vib}^{phase} = \frac{c}{4\pi f_0}\text{var}(\phi(k)) \quad (9)$$

and are respectively referred to herein as the "zero-crossing frequency estimator" and the "phase variance amplitude estimator."

For real-time tissue vibration imaging, only a short ensemble of ultrasound data (typically, 6-16 pulses or echoes) from each sample volume in a region of interest is available for processing. Conventional color-flow imaging systems utilize clutter filtering to suppress the clutter, while retaining the blood flow. However, due to the small number of temporal samples, the conventional clutter filtering-based approach, or a Fourier-based approach lacks sufficient resolution to discriminate between the tissue vibrations, blood flow, and clutter. A parametric approach that utilizes the characteristics of the vibration signal appears better suited to make this distinction. Three parametric approaches may be taken, based on the model of the ultrasound signal in Eqs. (6) and (7), including: (a) estimation of a pair of complex exponentials in noise; (b) autoregressive modeling; and, (c) decomposition of the phase of the ultrasound signal. In the following section, vibration detection algorithm based on these three parametric approaches are described in greater detail. One method of producing the complex ultrasound signal in Eq. (4) is a quadrature demodulation of the received ultrasound signal. An alternative method is to compute the time delays producing the phase variations in Eq. (4) by processing the received RF ultrasound data using a cross correlation technique.

Vibration Imaging Using Estimation of Complex Exponentials in Noise

Using the inverse Fourier transform of the Bessel expansion in Eq. (7), Eq. (6) is expanded, as follows:

$$y(\tau, m) = A'(\tau)\left\{e^{j2\pi f_0 \frac{2d_{tiss}(mT_{PRF})}{c}}\right\} \quad (10)$$

$$\left\{\sum_{n=-\infty}^{n=\infty} J_n(\beta)e^{j2\pi n f_{vib}T_{PRF} + jn\pi}\right\} + n(\tau, m)$$

$$= A'(\tau)e^{j2\pi f_0 \frac{2d_{tiss}(mT_{PRF})}{c}}$$

-continued $$\left\{\sum_{n=0}^{n=\infty} J_n(\beta)[e^{j2\pi n f_{vib}T_{PRF}} - e^{-j2\pi n f_{vib}T_{PRF}}]\right\} + n(\tau, m)$$

Thus, the ultrasound signal can be modeled as a sum of complex exponentials embedded in noise. As can be seen from the expression enclosed by square brackets in Eq. (10), vibrations correspond to matching pairs of complex exponentials. In contrast, the complex exponentials corresponding to clutter motion will typically not have such matching pairs of frequencies. The frequencies ($f_{tiss}, f_+, f_-$) may be estimated using the root-MUSIC and ESPRIT algorithms (disclosed by P. Stoica and R. Moses in "*Introduction to Spectral Analysis*," Upper Saddle River, N.J.: Prentice-Hall, 1997). Vibrations may then be detected using a matching peak criterion $|f_+ + f_- - 2f_{tiss}| < F_{threshold}$, and the vibration amplitude and frequency can be estimated using Eq (9), which is set forth above. The steps of the algorithm are described in more detail below, in regard to FIG. 3A. Based on this criterion, vibrations can be detected and distinguished from clutter motion. Any blood flow signals may be considered as part of the noise spectrum.

Figure 3A:
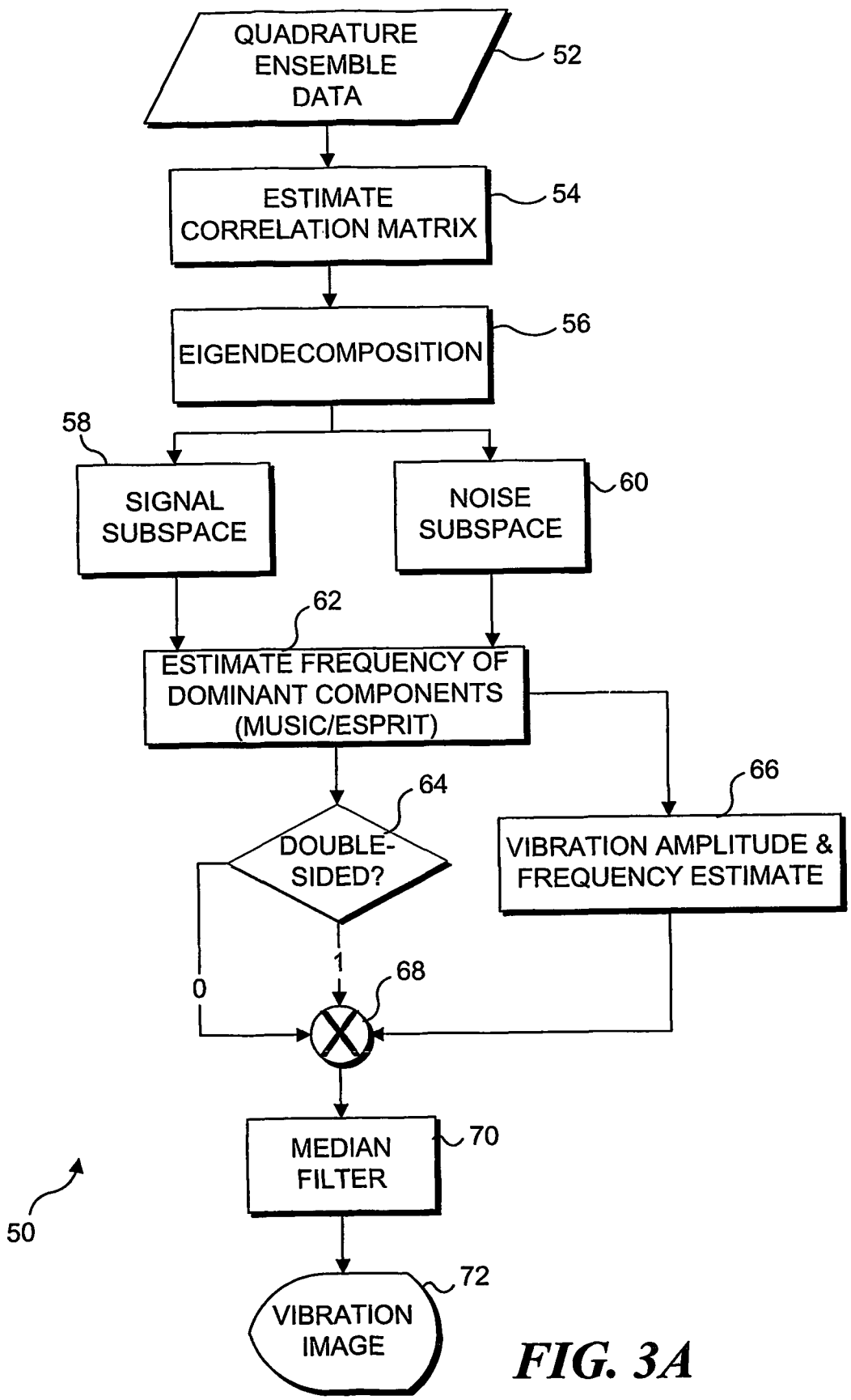
FIG. 3A is a flow chart showing the logical steps of a subspace-based algorithm for creating a vibrating tissue image in which bleeding is evident.

FIG. 3A illustrates a flow chart 50 that shows the logical steps involved in a first algorithm for estimating the tissue vibrations based upon a pair of complex exponentials in clutter or noise, that are normally excluded from color-flow processing. The procedure begins with a quadrature-demodulated ensemble of 2D ultrasound data 52.

In a step 54, a correlation matrix is estimated from the color-flow data. In a step 56, the correlation matrix is employed to carry out an eigendecomposition, producing a signal subspace 58 and a noise subspace 60. Using the signal subspace and the noise subspace, the frequency of the dominant components is estimated in a step 62, by employing the root-MUSIC and ESPRIT algorithms, as noted above. A decision step 64 then determines if each dominant component is double-sided, while a step 66 estimates the vibration amplitude and frequency of each dominant component using Eq. (8). If a dominant component is not double-sided (i.e., is not a potential tissue vibration component), decision step 64 returns a "zero," while if the dominant component is double-sided, the decision step return a one. A multiplier 68 then multiplies the output of decision step 64 times the vibration amplitude and frequency estimate for the dominant component, yielding a null if the dominant component is not a tissue vibration component and returning the estimate of vibration amplitude and frequency of the dominant component otherwise. A median filter 70 then filters isolated falsely-detected vibrations and other undesired noise from the results, so that the remaining vibration image indicating a bleeding site is displayed in a step 72.

Vibration Imaging Using an Autoregressive Signal Model

The ultrasound signal from vibrations can be modeled as the output of a $p^{th}$-order autoregressive linear prediction filter with white Gaussian noise having a variance $\sigma^2$, as the input, as follows:

$$y(\tau, m) = \sum_{k=1}^{p} a_{m-k}(\tau)y(\tau, m-k) + n(\tau, m) \quad (11)$$

The linear prediction coefficients, $\alpha_k(\tau)$, can be computed using either a least-squares minimization of the prediction errors or using the computationally-efficient Burg algorithm, as explained by Stoica and Moses in the above-referenced paper. A high-resolution spectral estimate can then be obtained from this autoregressive model as follows:

$$\|Y(\tau, f)\| = \frac{\sigma^2}{\left|1 + \sum_{k=1}^{p} a_k(\tau)e^{-j2\pi kf}\right|^2} \quad (12)$$

From Eq. (8), the presence of symmetric matching pairs of frequency peaks in the power spectrum around the clutter motion peak may be detected as a vibration. As before, any flow signals may be regarded as noise. For ultrasound signals from vibrations, the power spectrum in Eq. (13) will have frequency peaks ($f_{tiss}, f_+, f_-$) at the local minima of the polynomial $$A(\tau, f) = \left|1 + \sum_{k=1}^{p} a_k(\tau)e^{-j2\pi kf}\right|.$$

Vibrations can be detected using a matching peak criterion $|f_+ + f_- - 2f_{tiss}| < F_{threshold}$, and the vibration amplitude and frequency can be estimated using Eq. (9). The steps of this algorithm are described in more detail below, in connection with FIG. 3B.

Figure 3B:
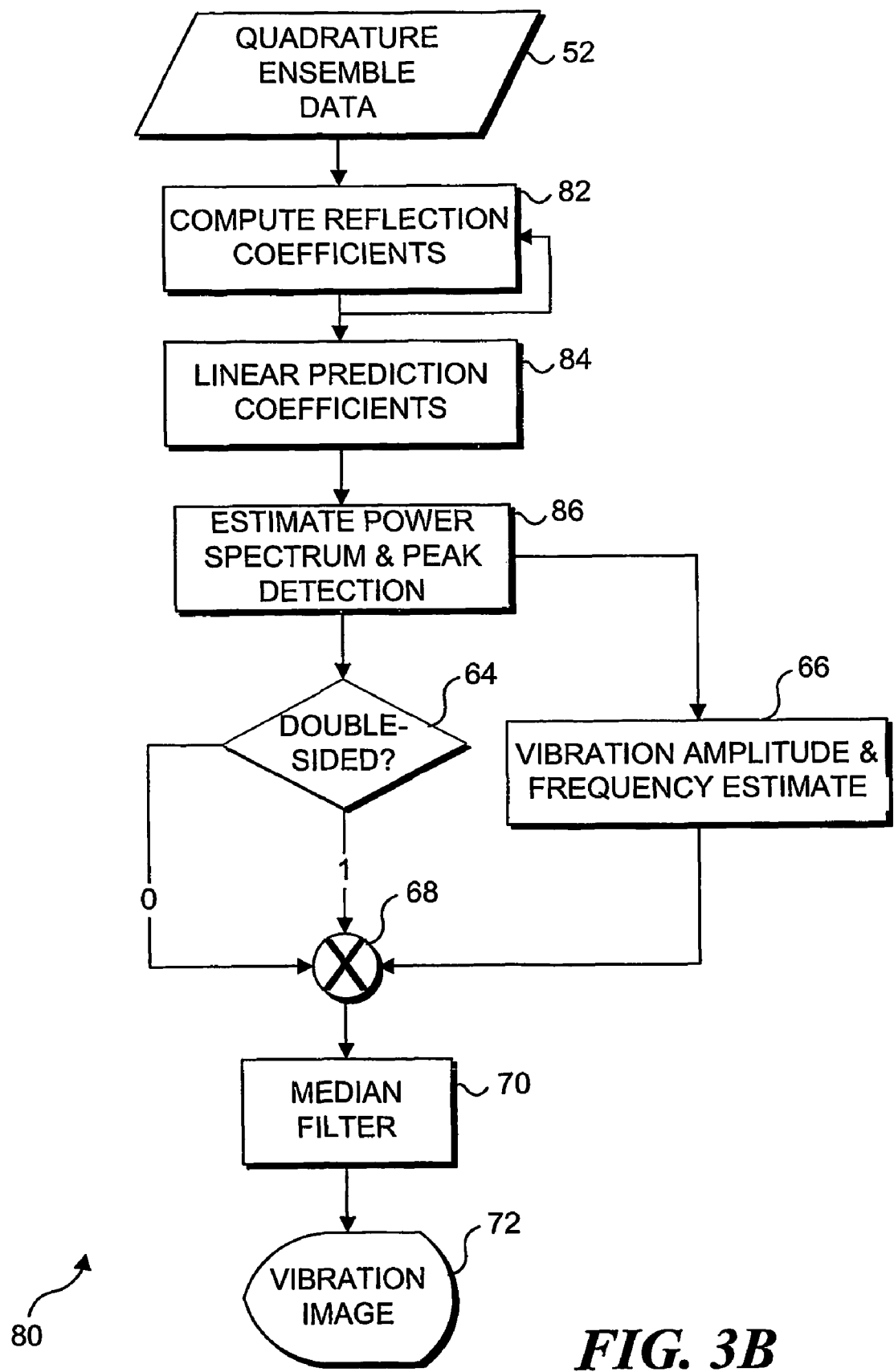
FIG. 3B is a flow chart showing the logical steps of an alternative algorithm that uses autoregression for creating a vibrating tissue image in which bleeding is evident.

As shown in a flow chart 80 in FIG. 3B, the second alternative algorithm also begins with quadrature-demodulated ensemble data set 52. In a step 82, reflection coefficients are computed for each ensemble of the quadrature-demodulated data. Using the reflection coefficients, linear prediction coefficients are determined in a step 84. In a step 86, the power spectrum is estimated from the linear prediction coefficients and the peaks in the power spectrum are detected. Again, decision step 64 determines if the peaks thus identified are for tissue vibration by determining if they are double-sided and returning a zero if not, and a one, if so. Also, step 66 provides for estimating the vibration amplitude and frequency at each of these peaks, and the results from decision step 64 are multiplied the estimated amplitude and frequency in multiplier 68. Median filter 70 is then applied to the results and the filtered image data are displayed as a vibration image, in step 72.

Vibration Imaging Based on Phase Decomposition

Another model of vibrations can be based on the phase ultrasound signal. As shown in Eq. (7), vibrations will produce an oscillatory signature in the phase, which will typically not be present in the case of clutter motion. Although flow signals may have oscillatory phase, the echoes from vibrating tissue are expected to be more coherent than those from flow. Thus, their phase may be modeled by a smaller number of dominant components. Accordingly, a vibration detection algorithm can also be based on decomposition of the phase of the ultrasound signal into its dominant components and testing for oscillatory phase. Alternatively, instead of using quadrature-demodulated ultrasound data, the phase can be estimated from RF ultrasound data by estimating the time delays between a pair of RF ultrasound data.

Any linear time-varying motion is first suppressed by down mixing the ensemble of 2D ultrasound data with the mean clutter velocity, estimated using the conventional autocorrelation method. The phase of the ensemble of 2D ultrasound data is then computed, and the mean phase is subtracted to suppress the effect of the stationary echo. The residual phase is then decomposed into its dominant components using a method similar to principal component analysis. The first step of the decomposition involves the estimation of the correlation matrix of the residual phase using the modified covariance method (Marple, 1987). An approximate eigendecomposition can then be performed using iterative QR factorization of the correlation matrix. The approximate eigenvalues, $\lambda_i$, may be estimated by the diagonal elements of the upper triangular matrix $R_k$ after the $k^{th}$ iteration. The eigenvectors are arranged in order of decreasing eigenvalues. The eigenvalues are a measure of the signal energy contributed by the corresponding eigenvector. Thus, the fraction of the total signal energy contained in the p dominant components can be estimated using $$E_p = \frac{\sum_{i=1}^{p} \lambda_i^2}{\sum_{i=1}^{N+1} \lambda_i^2}.$$

Figure 3C:
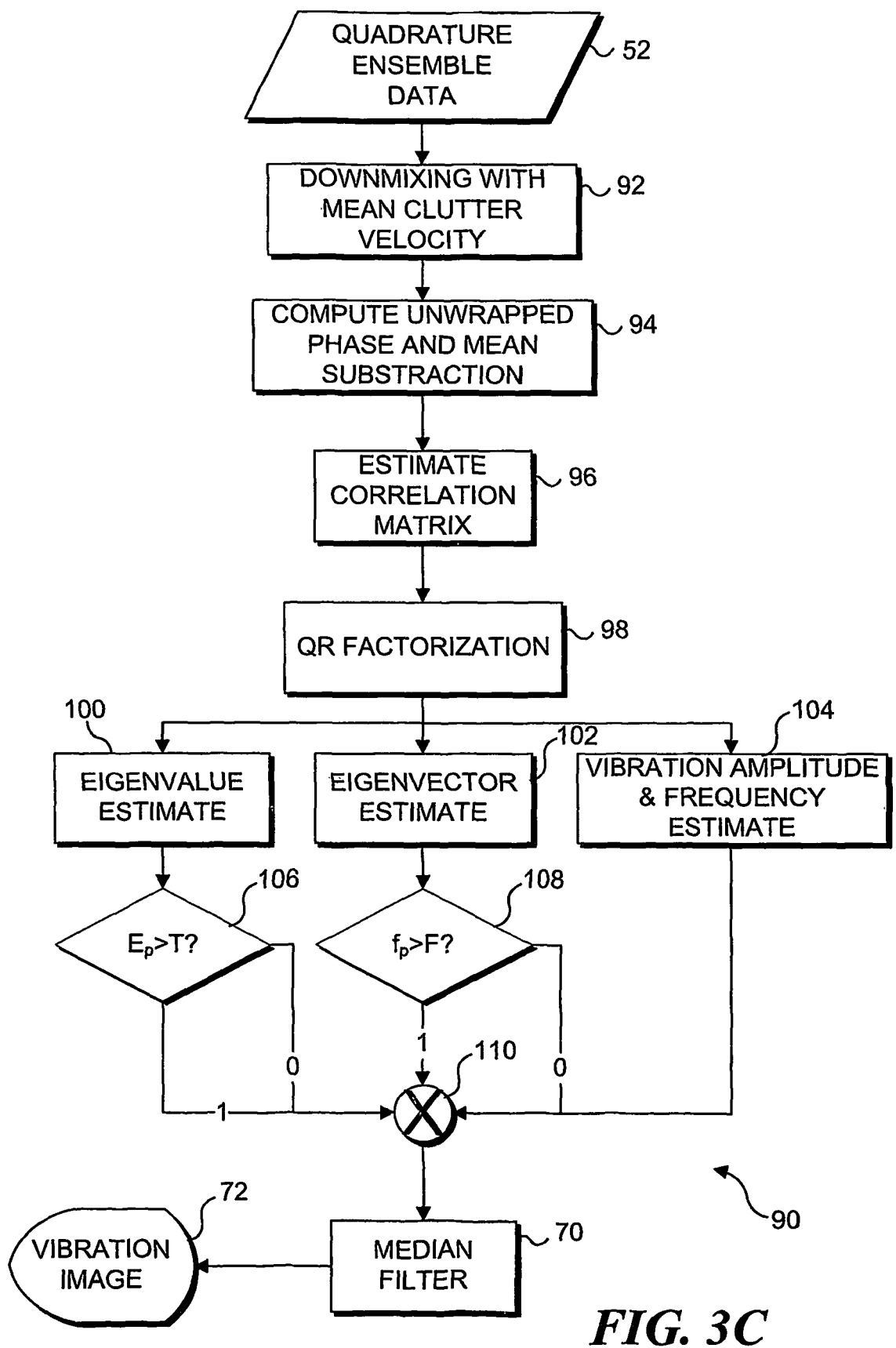
FIG. 3C is a flow chart showing the logical steps of yet another alternative algorithm that uses phase decomposition for creating a vibrating tissue image in which bleeding is evident.

Therefore, noise and blood flow can be suppressed using a threshold criterion, $E_p > E_{threshold}$. To further separate tissue vibrations from clutter motion, the fact that tissue vibrations have a higher frequency compared to clutter motion is applied. Vibrations can then be separated from clutter using a frequency threshold criterion $f_{vib} > F_{threshold}$, where $F_{threshold}$ is chosen so that at least one half of one period of the vibration is contained in an ensemble. The vibration frequency and amplitude may be estimated using Eq. (10). The steps of this algorithm are described in more detail below, in connection with FIG. 3C.

A flow chart 90 illustrates the logical steps of the third algorithm. Again, starting with the quadrature ensemble data, a step 92 down mixes the quadrature data with a mean clutter velocity, which is determined from the data. A step 94 provides for computing an unwrapped phase of the quadrature ensemble or color flow data, and then subtracting the mean clutter velocity from the unwrapped phase, resulting in a residual phase. As explained above, instead of determining the phase from quadrature-demodulated data, the phase can be determined from RF ultrasound data by estimating time delays between a pair of RF ultrasound data. Using the residual phase, a step 96 estimates a correlation matrix, which is then used to carry out a QR factorization in a step 98, yielding an eigenvalue estimate 100, an eigenvector estimate 102, and a vibration amplitude and frequency estimate 104, which are determined using Eq. (10), as noted above. Using the eigenvalue estimate, a decision step 106 determines if the total energy contained in the p dominant component is greater that a predefined threshold, T. If so, decision step 106 returns a zero if not, and a one if so. Similarly, a decision step 108 determines if the estimate eigenvector has a frequency that is greater than a predefined threshold, F. If so, decision step 108 returns a one, and if not, a zero. The results of decision steps 106 and 108, and the estimated vibration amplitude and frequency of the dominant components are then multiplied together by a multiplier 110, so that if either of the decision blocks has returned a zero, the result is null, but if neither has returned a zero, the estimated vibration amplitude and frequency from step 104 are returned. Again, median filter 70 is applied to the estimated amplitude and frequency, providing filtered results that are displayed as the vibration image, indicating a bleeding site, in step 72.

Detectable Vibration Amplitudes and Frequencies

In experiments using a physical phantom model, tissue vibrations with a peak amplitude of about 1 μm have been accurately detected. The minimum detectable vibration amplitude depends upon the noise level and dynamic range of the phase of the received ultrasound echo. In modern ultrasound machines, the phase can have a dynamic range of 96 dB or more (for 16-bit quadrature-demodulated data) and the signal exceeds the electronic and thermal noise level by typically 80 dB or more. Therefore, from Eq. (4), vibrations as small as 50 nm may theoretically be detected using ultrasound. Practically, the attenuation of the ultrasound signal will reduce the dynamic range and limit the minimum detectable amplitude in deep tissue to ~0.5 μm.

The detectable vibration frequencies depend upon the choice of PRF, i.e, on $F_{PRF}$. A PRF that is too low compared to the vibration frequency would lead to aliasing, while selecting a PRF that is too high will fail to detect low-frequency vibrations. A vibration can be detected only if at least half of one vibration cycle is captured within the temporal window corresponding to an ensemble. Thus, all vibrations with frequency between $$\frac{F_{PRF}}{2*E} \text{ and } \frac{F_{PRF}}{2}$$

can be detected theoretically without aliasing for an ensemble size E. Since vibrations can be broadband, a high-frequency vibration interrogated at a low PRF value can be mistaken for noise using this algorithm. Thus, for better sensitivity, it is desirable to select a PRF and an ensemble size so that only a few periods of the vibration are included in an ensemble. Accordingly, the maximum detectable frequency is $$\frac{kF_{PRF}}{E}$$

when k periods of the vibration are included in an ensemble. A simulation and phantom experiments that were carried out indicate that reliable detection may be performed using only one half to six vibration periods during the interrogation period. For example, with a PRF of 1 kHz and an ensemble size of 16, vibrations with frequency between 31.3 Hz and 375 Hz may be reliably detected.

Determination of Bleeding Rate

Since the tissue vibrations are produced by the blood flow eddies, the frequency of the tissue vibrations is the same as the frequency of the eddies. The Strouhal number (S) relates the frequency of eddies ($f_{vib}$) produced by an orifice to the diameter of the orifice (D), and the flow rate through the orifice (U), according to:

$$S = \frac{f_{vib} \times D}{U} \quad (13)$$

Since the Strouhal number remains constant, the vibration frequency can be related to the diameter of the orifice and the flow rate through the orifice. In addition, the energy in the eddies (E) and thus, the amplitude of the tissue vibrations ($\alpha_{vib}$), is directly proportional to the flow rate, as follows:

$$E \propto \alpha_{vib}^2 \propto U^2 \quad (14)$$

The bleeding rate $$Q = \frac{\pi \times D^2 \times U}{2}$$

can thus be determined from the frequency of the vibrations and the amplitude of the tissue vibrations.

Sources of Artifacts

In color-flow data acquisition, interrogation along each scan line is performed for only a brief period of time. Vibrations are transient, with typical durations of 10 ms-100 ms. Thus, there is a possibility that some vibrations may not be interrogated. Since the vibrations typically have a relatively large spatial extent and repeat every cardiac cycle, it is unlikely that the vibrations will be missed entirely; however, the spatial extent of the vibrations visible in the image may be only a part of the true spatial extent. By appropriately choosing the PRF and the region of interest, such discrepancies may be minimized.

Other artifacts may be falsely detected as vibrations. Transducer motion may introduce additional frequency peaks in the clutter spectrum and may cause false detections; however, these false detections may be minimized by using a trained sonographer to perform the scanning. Vibrations in the tensed skeletal muscle of the sonographer, and any ambient vibrations may be detected in the vibration image. In addition, the high-resolution spectral estimation methods may produce spurious peaks that can be falsely detected as vibrations. Such artifacts can be easily distinguished from pathological vibrations, which are expected to be correlated with the anatomy and periodic with every cardiac cycle. These artifacts can be also avoided if additional temporal samples are available. Any vibrations displayed in the vibration image should therefore be confirmed with the vibration spectrum by placing a Doppler sample volume at the location of the peak intensity.

Comparison of the Algorithms Derived from Modeling

The ability of the proposed algorithms to detect vibrations was evaluated using a simulation model. Simulations show that subspace-based algorithms such as MUSIC and ESPRIT have high sensitivity (96%) and specificity (98%) for detecting narrowband vibrations in the presence of clutter as well as blood flow and are robust even when broadband vibrations are present. For narrowband vibrations, an algorithm based on an autoregressive model has a slightly improved specificity (99%), a comparable sensitivity, and is robust to broadband vibrations. The phase decomposition-based algorithm has a slightly lower sensitivity (93%) and specificity (98%), but is more robust to broadband vibrations.

The computational requirements of the proposed algorithms are shown below in Table 2. The subspace-based algorithms (MUSIC/ESPRIT) have a computational requirement that is highly dependent on the choice of model order. In these algorithms, eigendecomposition is the most computationally-intensive task. The autoregression-based algorithm is less computationally intensive and the computational requirement is less dependent on the model order. In this case, the computation of the FFT for spectral estimation is the most computationally-intensive task. The phase decomposition method is the least computationally intensive, since it involves operations on real signals only. Thus, the phase-decomposition algorithm is most suitable for real-time implementation.

TABLE 1

Field II Simulation Parameters

| | |
|---|---|
| Center frequency | 5 MHz |
| PRF | 500 Horizontal |
| Transducer excitation | 5-period sinusoid |
| Transducer impulse response | Hanning-weighted 2-period sinusoid |
| fnumber | 2 |
| Number of elements | 192 |
| Transducer height | 15 mm |
| Element pitch | 0.4 mm |
| Element kerf | 0.03 mm |
| Transmit aperture | 25.6 mm |
| Receive aperture | 25.6 mm |
| Transmit focus | 40 mm |
| Receive focus | 30 mm to 100 mm in steps of 10 mm |
| Elevation focus | 20 mm |
| Mathematical element size | 0.37 mm × 1.5 mm |
| Sampling frequency | 105 MHz |
| Sound velocity | 1540 m/s |
| Number of scan lines | 32 |
| Number of ensembles | 10 |

TABLE 2

Computational requirement (million operations/sec) for real-time imaging at 10 frames/s with 32 scan lines, 256 samples/scan line, and ensemble 10

| | Model Order | | |
|---|---|---|---|
| Algorithm | p = 2 | p = 3 | p = 4 |
| MUSIC | — | 3631 | 7653 |
| ESPRIT | — | 2218 | 6455 |
| AR | — | 1606 | 1630 |
| Phase-decomposition | 181 | 489 | 1107 |
| Color flow | | 89 | |

In Vivo Empirical Tests of Arterial and Organ Bleeding in Animal Model

FIG. 5A illustrates a color-flow image of a punctured femoral artery. A dotted line box indicates the region of interest. An arrow indicates the approximate location of a puncture. In FIG. 5B, a vibration amplitude image of the punctured femoral artery is illustrated. Although not visible in color in this grayscale image, the vibrations at the puncture site in the original color image appear green relative to the shades of gray in the surrounding tissue. Similarly, in FIG. 5C, a vibration frequency image shows low-frequency vibrations in color at the puncture site, relative to shades of gray for the surrounding tissue.

Figure 4:
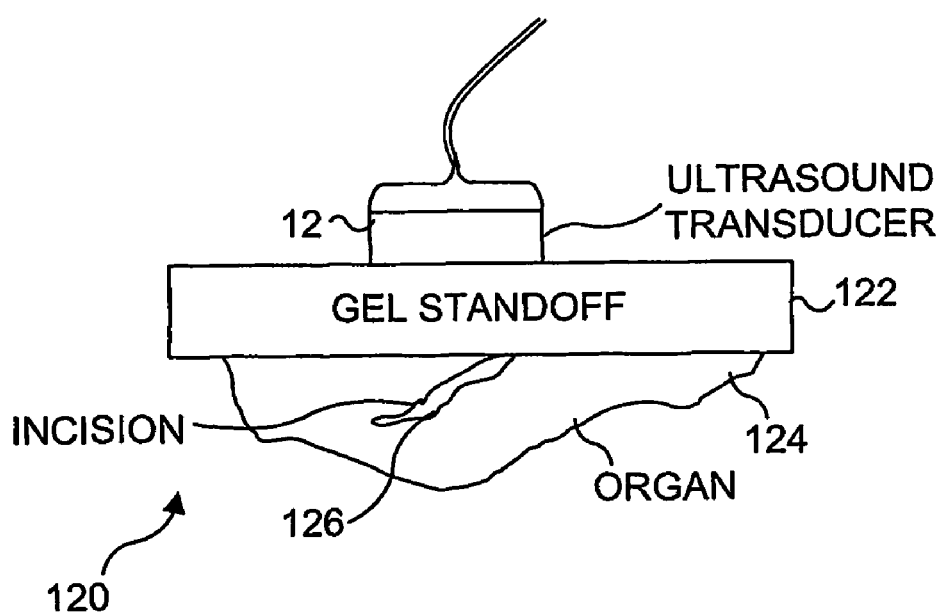
FIG. 4 is a schematic diagram showing how a gel standoff is used for acoustically coupling an ultrasound transducer to an organ that is exposed and incised to create a bleeding site.

FIG. 4 is a schematic view 120 that illustrates how ultrasound transducer 12 is employed to produce color-flow data for an incised organ 124. To couple acoustic signals from and to the ultrasound transducer, a gel standoff 122 is disposed between the ultrasound transducer and the exposed organ. The gel standoff provides an efficient couple between the tissue of the organ and the transducer. In this manner, tissue vibrations caused by bleeding through an incision 126 can readily be produced in accord with the present invention.

In FIG. 6A, a color-flow image of an incised spleen is shown. An arrow indicates the pooled blood from an incision, where the blood pool has accumulated between the organ and the gel stand-off. Some blood flow is observed at the bleeding site as indicated by an arrow. FIG. 6B shows the vibration amplitude image, where vibrations surrounding the bleeding site are indicated by an arrow. A vibration frequency image in FIG. 6C shows the low-frequency vibrations in color to indicate the bleeding site.

FIG. 7A shows the color-flow image of an incised liver in a rabbit. The liver was surgically exposed and a triangular incision was made with a scalpel, causing moderate bleeding. The liver was imaged though a gel standoff. The location of the incision is clearly seen in the B-mode image (not shown), and some flow is observed in the artery feeding the bleed. However, from the color-flow image, it is not possible to identify the bleeding site at the incision. The vibration amplitude image is shown in FIG. 7B. Vibrations are clearly observed surrounding the incision from which bleeding is occurring, as indicated by an arrow. The vibration frequency image in FIG. 7C shows low-frequency vibrations, and the bleeding site is again clearly visible (although not so apparent in this grayscale image as in the original color images). The vibration image and color-flow images therefore provide complementary information and a clear correlation between the spatial location of the vibration, and the underlying anatomy can be observed. Thus, a combination of B-mode, color-flow, and tissue vibration images can be a powerful diagnostic tool for detecting the location of internal bleeding.

Summary

Empirical evidence demonstrates the feasibility of real-time ultrasound imaging of low-intensity local vibrations in the vessel wall and surrounding tissue associated with punctured arteries and organ bleeds. Several algorithms based on parametric signal decomposition and spectral estimation have been developed for imaging small-amplitude tissue vibrations using as few as 10 temporal samples. The vibration amplitude and frequency can be estimated accurately, and real-time tissue vibration imaging has been implemented on an ultrasound machine with a software-programmable subsystem.

Tissue vibration imaging can provide additional diagnostic information that is currently not available to the clinician using conventional tools. An ultrasound device with tissue vibration imaging capability can become a useful screening and diagnostic tool for paramedics and trauma centers for rapid diagnosis and localization of active internal bleeding. Such real-time localization of bleeding can then be employed for targeting and evaluating the effects of HIFU and other therapies intended to stop the bleeding.

Although the present invention has been described in connection with the preferred form of practicing it and modifications thereto, those of ordinary skill in the art will understand that many other modifications can be made to the present invention within the scope of the claims that follow. Accordingly, it is not intended that the scope of the invention in any way be limited by the above description, but instead be determined entirely by reference to the claims that follow.

The invention in which an exclusive right is claimed is defined by the following:

1. Apparatus for detecting bleeding at an internal site using ultrasound, comprising:
   (a) an ultrasound transducer
   (b) a control system coupled to the ultrasound transducer to control its operation; and
   (c) a tissue vibration processor that processes the ultrasound to identify tissue vibrations caused by internal bleeding, producing a signal indicating the internal bleeding,
   wherein the tissue vibration processor configured to identify the tissue vibrations, producing a tissue vibration signal, and filters the tissue vibration signal, producing a filtered signal from which any contribution to the tissue vibration from a source other than bleeding at the internal site has been substantially minimized, and wherein the tissue vibration processor configured to identify tissue vibrations at the internal site by:
(a) estimating a correlation matrix from the color-flow signal;
(b) carrying out an eigen decomposition of the correlation matrix to identify a signal subspace and a noise subspace;
(c) estimating a frequency of dominant vibration components in the signal subspace and the noise subspace; and
(a) based upon an estimate of the frequency of the dominant vibration components, determining a vibration amplitude estimate and a vibration frequency estimate, at least one of the vibration amplitude estimate and the vibration frequency estimate comprising the tissue vibration signal.

2. The apparatus of claim 1, wherein the tissue vibration processor configured to filter the tissue vibration signal by filtering out clutter and noise at frequencies that are substantially lower than an expected frequency range of tissue vibrations corresponding to bleeding at the site.

3. The apparatus of claim 1 wherein the tissue vibration processor filters the tissue vibration signal by filtering out clutter and noise at frequencies that are substantially higher than an expected frequency range of tissue vibrations corresponding to bleeding at the site.

4. The apparatus of claim 1, wherein the tissue vibration processor further configured to confirm that vibrations displayed in the vibration image correspond to bleeding at the site by placing a Doppler sample volume at a location of the tissue vibration, producing a tissue vibration spectrum.

5. The apparatus of claim 1, wherein the display configured to present at least one of a vibration amplitude image and a vibration frequency image of the internal site.

6. The apparatus of claim 1 further comprising a B-mode processor that configured to produce a grayscale image showing underlying anatomy of the internal site, so that the display selectively presents at least one of a B-mode image of the internal site and the tissue vibration image of the internal site, substantially in real time.

7. The apparatus of claim 1 further comprising a color-flow processor, so that the display configured to selectively present at least one of a color-flow image of the internal site and the tissue vibration image of the internal site.

8. The apparatus of claim 1 further comprising a Doppler processor.

9. Apparatus for detecting bleeding at an internal site using ultrasound, comprising:
(a) an ultrasound transducer
(b) a control system coupled to the ultrasound transducer to control its operation; and
(c) a tissue vibration processor that processes the ultrasound to identify tissue vibrations caused by internal bleeding, producing a signal indicating the internal bleeding,
wherein the tissue vibration processor configured to identify the tissue vibrations, producing a tissue vibration signal, and filters the tissue vibration signal, producing a filtered signal from which any contribution to the tissue vibration from a source other than bleeding at the internal site has been substantially minimized,
and wherein the tissue vibration processor configured to identify tissue vibrations at the internal site by:
(a) computing reflection coefficients from the color-flow signal;
(b) computing linear prediction filter coefficients from the reflection coefficients;
(c) estimating a power spectrum and detecting peaks in the power spectrum; and
(d) based upon an estimate of the power spectrum and the peak, determining a vibration amplitude estimate and a vibration frequency estimate, at least one of the vibration amplitude estimate and the vibration frequency estimate comprising the tissue vibration signal.

10. Apparatus for detecting bleeding at an internal site using ultrasound, comprising:
(a) an ultrasound transducer
(b) a control system coupled to the ultrasound transducer to control its operation; and
(c) a tissue vibration processor that processes the ultrasound to identify tissue vibrations caused by internal bleeding, producing a signal indicating the internal bleeding,
wherein the tissue vibration processor configured to identify the tissue vibrations, producing a tissue vibration signal, and filters the tissue vibration signal, producing a filtered signal from which any contribution to the tissue vibration from a source other than bleeding at the internal site has been substantially minimized,
and wherein the tissue vibration processor configured to identify tissue vibrations at the internal site by:
(a) estimating a mean clutter velocity from the color-flow signal, using autocorrelation;
(b) down mixing the color-flow signal with the mean clutter velocity, producing a down mixed signal;
(c) computing a phase of the down mixed signal and a mean phase of the down mixed signal;
(d) subtracting the mean phase from the phase of the down mixed signal, producing a residual phase;
(e) decomposing the residual phase into its dominant components; and
(f) applying energy and frequency thresholds to substantially suppress any contribution to the tissue vibration due to noise and blood flow, yielding an estimate of vibration amplitude and vibration frequency of tissue.

11. The apparatus of claim 10, wherein the tissue vibration processor further configured to decompose the residual phase by:
(a) estimating a correlation matrix from the residual phase; and
(b) performing eigendecompostiion of the correlation matrix to determine the dominant components.

* * * * *